| United States Patent [19] | [11] Patent Number: 5,053,539 |
| Yano et al. | [45] Date of Patent: Oct. 1, 1991 |

[54] METHYLENE-CROSSLINKED POLYARYLAMINE AND PROCESS FOR PREPARING SAME

[75] Inventors: Naoyuki Yano; Tatsuya Nagayoshi; Takashi Nagou; Zunzi Tashima; Noritoshi Ishida; Hiroyuki Itoh; Katsuyuki Nagamatsu, all of Ohmuta, Japan

[73] Assignee: Mitsui Toatsu Chemicals, Incorporated, Tokyo, Japan

[21] Appl. No.: 642,338

[22] Filed: Jan. 17, 1991

[30] Foreign Application Priority Data

Apr. 11, 1990 [JP] Japan .................................. 2-94065

[51] Int. Cl.$^5$ .......................................... C07C 211/00
[52] U.S. Cl. .................................................. 564/333
[58] Field of Search ................................ 564/333, 331

[56] References Cited

U.S. PATENT DOCUMENTS 3,274,274  3/1966  Repper et al. ...................... 563/333

*Primary Examiner*—Alan Siegel
*Assistant Examiner*—Jessica H. Nguyen
*Attorney, Agent, or Firm*—Millen, White & Zelano

[57] ABSTRACT

A methylene-crosslinked polyarylamine is disclosed which contains a less amount of N-methylmethylenedianiline. A process for continuously preparing this kind of methylene-crosslinked polyarylamine is also revealed which comprises reacting aniline with formalin in the presence of hydrochloric acid under specific reaction conditions.

2 Claims, No Drawings

METHYLENE-CROSSLINKED POLYARYLAMINE AND PROCESS FOR PREPARING SAME

BACKGROUND OF THE INVENTION (i) Field of the Invention

The present invention relates to a process for continuously preparing a methylene-crosslinked polyarylamine.

More specifically, the present invention is directed to a process for the continuous preparation of a methylene-crosslinked polyarylamine from aniline and formalin by the use of a multi-stage reactor, the aforesaid process being characterized by reacting aniline with formalin in the presence of hydrochloric acid under conditions that formalin is divided and placed in 3 or more stages; hydrochloric acid is used in a molar ratio of from 0.1 to 0.5 mole per mole of aniline; aniline is used finally in a molar ratio of from 1.5 to 4.0 moles per mole of formalin; reaction temperatures in the first stage, the second stage, the third et seq. stages and the final stage are adjusted to 20–50° C., 40–70° C., 50–90° C. and 110° C. or more, respectively; and molar ratios of water to aniline are 1.3–2.5 in the first stage, 1.9–5.0 in the second stage, and 2.4–5.7 in the third et seq. stages.

The methylene-crosslinked polyarylamine obtained by the present invention (hereinafter referred to as ["poly (MDA)"]will be reacted with phosgene to produce a polyisocyanate, and this polyisocyanate will be used as a raw material for polyurethane resins such as hard and semi-hard foams and elastomers.

The methylene-crosslinked polyarylamine can be represented by the formula (I)

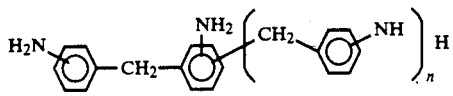

wherein n is 0 or more.

(ii) Description of the Related Art

In general, it is known that a polyisocyanate prepared from the above-mentioned raw materials is less reactive, when the content of a hydrolyzable chlorine compound is high.

In case that the polyisocyanate containing a large amount of the hydrolyzable chlorine compound is polymerized with a polyamine or a polyol and used as a polyurethane resin, a reaction rate is low, and thus it is utilized as a known means to increase the amount of a catalyst for urethane production such as a tertiary amine or an organic metal for the acceleration of the reaction rate. In this case, a curing rate can be increased, but unpreferably, a bodying speed is also accelerated, with the result that a pot life shortens and an expansion ratio decreases.

Therefore, the polyisocyanate containing a less amount of the hydrolyzable chlorine compound is very useful as the raw material of the urethane, and it is preferred that the content of the hydrolyzable chlorine compound is 0.18% or less in terms of chlorine (the same shall apply hereinafter).

Japanese Patent Publication No. 50-38095 discloses that a polyamine containing a large amount of an amino group can be continuously prepared by the use of a multi-stage reactor in which each of the stages is adjusted in a certain temperature range, and that formalin is divided and placed in the two or more stages so as to change a molar ratio of the raw material amine to formalin in the respective stages, whereby the distribution of polyamine nuclei can be controlled.

However, this publication does not have the description regarding how to decrease the content of the hydrolyzable chlorine compound. In a tracing test of the present inventors, a continuous reaction was carried out under conditions that formalin was divided and placed in two stages, the molar ratio of aniline/formalin was 1.8, the molar ratio of hydrochloric acid/aniline was 0.5, and the reaction temperature of the last reaction stage was adjusted to 100° C, and as a result, the content of N-methylmethylenedianiline (hereinafter referred to as "N-methyl-MDA") was 0.35%. Furthermore, this N-methyl-MDA was reacted with phosgene to produce a polyisocyanate. In this case, the hydrolyzable chlorine compound in the thus produced polyisocyanate contained 0.42% of chlorine. Accordingly, the problem to be solved is to decrease the amount of a precursor which will change into the hydrolyzable chlorine compound in the poly(MDA) in the multi-stage reaction.

SUMMARY OF THE INVENTION

The present inventors have intensively researched, and as a result, they have found that most of a hydrolyzable chlorine compound contained in a polyisocyanate is attributed to N-me&hyl-MDA contained as an impurity in the raw material poly(MDA), N-methylpolyphenylpolyamine and a reaction intermediate. In addition, it can be supposed that the above-mentioned N-methyl-MDA is formed as follows: A side reaction between aniline and formaldehyde produces N-methylaniline, and this by-product reacts, like aniline, with formaldehyde to become N-methyl-MDA. In this connection, it has been found that the above-mentioned side reaction is inhibited by decreasing the amount of hydrochloric acid and lowering the molar ratio of formaldehyde/aniline.

The present inventors have conducted further researches on the basis of this knowledge, and they have established a process for the continuous preparation of the poly(MDA) containing less amounts of N-methyl-MDA and a reaction intermediate, this process being characterized by reacting aniline with formalin in the presence of hydrochloric acid under the conditions that the amount of hydrochloric acid is in the range of from 0.1 to 0.5 mole per mole of aniline; formalin is divided and placed in three or more stages; molar ratios of water to aniline are 1.3–2.5 in the first stage, 1.9–5.0 moles in the second stage and 2.4–5.7 in the third stage et seq.; and reaction temperatures are adjusted to 20–50° C. in the first stage, 40–70° C. in the second stage, 50–90° C. in the third stage et seq. and 110° C. or more in the last stage. The present invention has been completed in accordance with the above-mentioned conception.

That is, the present invention is directed to a process for preparing a methylene-crosslinked polyarylamine by reacting aniline with formalin in the presence of hydrochloric acid under the following conditions (a), (b), (c) and (d):

(a) the amount of hydrochloric acid is in the range of from 0.1 to 0.5 mole per mole of aniline;

(b) the amount of aniline is in the range of from 1.5 to 4.0 moles per mole of formalin;

(c) the reaction is divided in at least four stages, and the reaction in the first stage is carried out at 20 to 50° C. in a water/aniline ratio in the range of from 1.3 to 2.5 moles, the reaction in the second stage is done at 40 to 70° C. in a water/aniline ratio in the range of from 1.9 to 5.0 moles, the reaction in the third stage is done at 50 to 90° C. in a water/aniline ratio in the range of from 2.4 to 5.7 moles, and the reaction in the last stage is done at a temperature of 110° C. or more; and (d) formalin is divided into 3 or more stages and used in the reactions in the respective stages.

DESCRIPTION OF THE PREFERRED EMBODIMENTS

Now, the present invention will be described in detail.

The first reactor is fed with the total amount of hydrochloric acid which is used in a reaction and partial amounts of aniline and formalin.

It is a preferable manner to feed formaldehyde in the form of a mixture of the same and hydrochloric acid, because formaldehyde tends to condense with aniline to form a solid which is nearly insoluble in an aqueous aniline hydrochloride solution. If highly concentrated formalin is handled or placed in the first reactor, a formalin introduction inlet tends to be clogged with the formed solid, and when the solid grows, a solution feed pipe extending to the second reactor is also clogged with the grown solid, so that the continuous reaction is impeded.

Furthermore, formalin can be diluted with water and then introduced into the first reactor, but the use of much water leads to the deterioration of volumetric efficiency. In addition, an aqueous layer is separated from an oil layer, so that a reaction solution is not in a uniform state, which makes a continuous operation difficult. For these reasons, it is preferable that formalin is used at the highest possible concentration.

In the first reactor, neutralization heat of aniline and hydrochloric acid and condensation heat of aniline and formalin are generated, and therefore a cooling device such as a jacket cooling device or an external cooling device is necessary.

When the reaction temperature is 20° C. or less, the condensate of aniline and formaldehyde becomes a slurry state, and the dispersibility of the reaction solution declines. As a result, N-methyl-MDA is easily formed and the inlet for the mixture of formalin and hydrochloric acid also tends to be clogged unpreferably.

Furthermore, the elevation of the reaction temperature leads to the increase of the unpreferable side reaction, particularly the increase of N-methyl-MDA.

Therefore, it is necessary that the reaction temperature in the first reactor is in the range of from 20 to 50° C., preferably from 20 to 40° C.. The remaining formalin is divided and fed to at least two second et seq. reactors.

In the second et seq. reactors, formalin must be fed at a concentration of from 10 to 25%, because when the concentration of formalin is high, the feed inlet tends to be clogged, and when that of formalin is low, the reaction solution cannot take a uniform phase.

The amount of formalin which is fed to each reactor can be optionally selected, but it is preferred that 20 to 60% of the total formalin is fed to the first reactor, 20 to 50% thereof to the second reactor, and 10 to 40% thereof to the third et seq. reactors. In order to bring the reaction to an end, formalin should not be fed to the last reactor.

The temperatures of the respective reactors should be adjusted so as to control the production of the solid and to inhibit the side reaction, and hence the temperature of the first reactor is from 20 to 50° C., that of the second reactor is from 40 to 70° C., and that of the third et seq. reactors is from 50 to 90° C. Preferably, the temperature of the first reactor is from 20 to 40° C., that of the second reactor is from 40 to 60° C., and that of the third et seq. reactors is from 50 to 80° C.

When the temperature in the third et seq. reactors except the first, second and final reactors is less than the lower limit of the above-mentioned reaction temperature range, the reaction solution becomes a slurry state, and when it is in excess of the upper limit thereof, the production of N-methyl-MDA increases unpreferably.

In order to bring the reaction to an end, the temperature of the final reactor should be adjusted to 110° C. or more.

However, if the reaction temperature is too high, the unpreferable side reaction occurs, and thus the upper limit of the reaction temperature is preferably adjusted to 150° C.

If the reaction solution contains a less amount of water, the solid is formed, so that the reaction solution becomes a slurry state. Conversely, if an excessive amount of water is present in the reaction solution, an aqueous phase is separated from an oil phase, so that a reaction solution is not in a uniform. Therefore, the concentrations of formalin which is fed to the respective stages should be adjusted so that the molar ratios of water to the raw material amine are from 1.3 to 2.5 in the first reactor, from 1.9 to 5.0 in the second reactor and from 2.4 to 5.7 in the final reactor, whereby the formation of the solid can be prevented and the dispersibility and fluidity of the reaction solution can be kept good.

That is, in case that hydrochloric acid having a concentration of 35% is used, the concentrations of formalin which is fed to the first reactor and the second et seq. reactors should be adjusted to 30% or more and 10–25%, respectively.

Finally, the molar ratio of aniline to formalin is in the range of from 1.5 to 4.0, preferably from 1.8 to 3.0, and the molar ratio of hydrochloric acid to aniline is in the range of from 0.1 to 0.5, preferably from 0.2 to 0.4.

The number of the stages in the multi-stage reactor is usually from 4 to 10, and the residence time of the reaction solution in each stage is suitably from 20 to 90 minutes and the total residence time is suitably from about 1.5 to about 10 hours.

The reaction solution is allowed to reside and is stirred for a certain time in each stage, and it is then transferred to the next stage, whereby the reaction proceeds. Afterward, the reaction solution is taken out through the outlet of the final reactor. The taken reaction solution is neutralized with an alkali, washed with water, dehydrated, and then subjected to an aniline removal treatment.

The thus obtained methylene-crosslinked polyarylamine contains a less amount, 0.18% or less, of N-methylmethylenedianiline which is the cause of the hydrolyzable chlorine compound in the polyisocyanate which can be prepared by the reaction with phosgene, and in fact, the hydrolyzable chlorine compound in the polyisocyanate which was prepared by the reaction with phosgene was 0.18% or less.

According to the present invention, a methylene-crosslinked polyarylamine can be provided in which the content of N-methyl-MDA is 0.18% or less, and this kind of methylene-crosslinked polyarylamine is suitable for the preparation of a polyisocyanate in which the content of a hydrolyzable chlorine compound is low. The other effects of the present invention are that, though the molar ratio of hydrochloric acid to the raw material amine can be limited to a low level, no solid precipitates and workability is good, and that formalin having a relatively high temperature can be fed to the second et seq. reactors and thus a cooling cost is low. In consequence, it is fair to say that the present invention is industrially valuable.

Now, the present invention will be described in detail in reference to examples. It is to be noted that these examples are for the elucidation of the present invention and do not intend to limit the scope of the present invention.

EXAMPLE 1

A four-stage tank type reactor was used in which effective volumes of the first, second, third and fourth stages were 300 ml, 300 ml, 500 ml and 550 ml, respectively, and the rotational frequency of stirring in each stage was 700 rpm.

The first stage of the reactor was fed with aniline at 327 g/hr, 35% hydrochloric acid at 165 g/hr and 43% formalin at 34 g/hr (33% of the total formalin), hydrochloric acid and formalin being previously mixed, and the second stage and the third stage were each fed with 22% formalin at 67 g/hr (33% of the total formalin) by means of a quantitative pump.

Reaction temperatures in the first, second, third and fourth stages were adjusted to 30° C., 50° C., 65° C. and 120° C., respectively, by means of an external cooler and by heating.

Eight hours after the feed start of the raw materials, the composition of the reaction solution became a steady state, and at this time, a part of the reaction solution was sampled from the fourth stage. The sample was then neutralized with a 32% aqueous caustic soda solution, and an oil layer was separated at 70 to 80° C. and then washed with warm water in an about 1.5-fold amount. Afterward, aniline and water were distilled off under reduced pressure.

The content of N-methylmethylenedianiline in the resulting poly(MDA) was 0.13%.

This polyamine was reacted with phosgene in accordance with a usual cold and warm two-stages process to obtain a polyisocyanate. The content of a hydrolyzable chlorine compound in this polyisocyanate was 0.10%.

EXAMPLE 2

The same reactor as in Example 1 was used.

Afterward, the same procedure as in Example 1 was effected except that the first stage of the reactor was fed with 95% aniline at 345 g/hr, 35% hydrochloric acid at 110 g/hr and 43% formalin at 27 g/hr (33% of the total formalin), hydrochloric acid and formalin being previously mixed, and the second stage and the third stage were each fed with 22% formalin at 52.8 g/hr (33% of the total formalin) by means of a quantitative pump.

The content of N-methylmethylenedianiline in the resulting poly(MDA) was 0.10%.

This polyamine was reacted with phosgene in accordance with a usual cold and warm two-stages process to obtain a polyisocyanate. The content of a hydrolyzable chlorine compound in this polyisocyanate was 0.09%.

EXAMPLE 3

The same reactor as in Example 1 was used.

Afterward, the same procedure as in Example 1 was effected except that the first stage of the reactor was fed with 95% aniline at 345 g/hr, 35% hydrochloric acid at 110 g/hr and 43% formalin at 41 g/hr (50% of the total formalin), hydrochloric acid and formalin being previously mixed, the second stage was fed with 22% formalin at 48 g/hr (30% of the total formalin), and the third stage was fed with 22% formalin at 32 g/hr (20% of the total formalin) by means of a quantitative pump.

The content of N-methylmethylenedianiline in the resulting polyamine was 0.12%.

This poly(MDA) was reacted with phosgene in accordance with a usual cold and warm two-stages process to obtain a polyisocyanate. The content of a hydrolyzable chlorine compound in this polyisocyanate was 0.09%.

EXAMPLE 4

A five-stage tank type reactor was used in which effective volumes of the first, second, third, fourth and fifth stages were 300 ml, 300 ml, 300 ml, 500 ml and 550 ml, respectively, and the rotational frequency of stirring in each stage was 700 rpm.

The first stage of the reactor was fed with 95% aniline at 345 g/hr, 35% hydrochloric acid at 110 g/hr and 43% formalin at 41 g/hr (50% of the total formalin), hydrochloric acid and formalin being previously mixed, the second stage was fed with 22% formalin at 48 g/hr (30% of the total formalin), the third stage and fourth stages were each fed with 10% formalin at 35 g/hr (10% of the total formalin) by means of a quantitative pump.

The same procedure as in Example 1 was effected except that reaction temperatures in the first, second, third, fourth and fifth stages were adjusted to 30° C., 50° C., 65° C., 65° C. and 120° C., respectively, by means of an external cooler and by heating.

The content of N-methylmethylenedianiline in the resulting polyamine was 0.08%.

This polyamine was reacted with phosgene in accordance with a usual cold and warm two-stages process to obtain a polyisocyanate. The content of a hydrolyzable chlorine compound in this polyisocyanate was 0.09%.

EXAMPLE 5

The same reactor as in Example 4 was used.

The first stage of the reactor was fed with 95% aniline at 345 g/hr, 35% hydrochloric acid at 110 g/hr and 43% formalin at 41 g/hr (50% of the total formalin), hydrochloric acid and formalin being previously mixed, the second stage was fed with 22% formalin at 48 g/hr (30% of the total formalin), the third stage was fed with 22% formalin at 32 g/hr (20% of the total formalin) by means of a quantitative pump. Reaction temperatures in the first, second, third, fourth and fifth stages were adjusted to 30° C., 50° C., 90° C., 90° C. and 120° C., respectively, by means of an external cooler and by heating.

The content of N-methylmethylenedianiline in the resulting polyamine was 0.13%.

This poly(MDA)) was reacted with phosgene in accordance with a usual cold and warm two-stages process to obtain a polyisocyanate. The content of a hydrolyzable chlorine compound in the polyisocyanate was 0.12%.

COMPARATIVE EXAMPLE 1

The same reactor as in Example 1 was used.

The first stage of the reactor was fed with 95% aniline at 345 g/hr, 35% hydrochloric acid at 209 g/hr and 43% formalin at 94 g/hr (80% of the total formalin), and the second stage was fed with 43% formalin at 23 g/hr (20% of the total formalin) by means of a quantitative pump.

The same procedure as in Example 1 was effected except that reaction temperatures in the first, second, third and fourth stages were adjusted to 30° C., 30° C., 100° C. and 100° C., respectively, by means of an external cooler and by heating.

The content of N-methylmethylenedianiline in the resulting polyamine was 0.29%.

This poly(MDA) was reacted with phosgene in accordance with a usual cold and warm two-stages process to obtain a polyisocyanate. The content of a hydrolyzable chlorine compound in this polyisocyanate was 0.25%.

COMPARATIVE EXAMPLE 2

The same reactor as in Example 1 was used.

The first stage of the reactor was fed with 95% aniline at 345 g/hr, 35% hydrochloric acid at 95 g/hr and 43% formalin at 75 g/hr (70% of the total formalin), and the second stage was fed with 43% formalin at 32 g/hr (30% of the total formalin) by means of a quantitative pump.

The same procedure as in Example 1 was effected except that reaction temperatures in the first, second, third and fourth stages were adjusted to 65° C., 75° C., 00° C. and 100° C., respectively, by means of an external cooler and by heating.

The content of N-methylmethylenedianiline in the resulting polyamine was 0.44%.

This polyamine was reacted with phosgene in accordance with a usual cold and warm two-stages process to obtain a polyisocyanate. The content of a hydrolyzable chlorine compound in this polyisocyanate was 0.30%.

COMPARATIVE EXAMPLE 3

A five-stage continuous reactor was used in which effective volumes of all the reaction tanks were 300 ml and the rotational frequency of stirring in each stage was 700 rpm.

The first stage of the reactor was fed with aniline at 296.4 g/hr, 37.1% formalin at 71.4 g/hr and 36.1% hydrochloric acid at 160.8 g/hr, and the second stage was fed with 37.1% formalin at 71.4 g/hr by means of a quantitative pump.

Reaction temperatures in the first, second, third, fourth and fifth stages were adjusted to 30° C., 30° C., 60° C., 90° C. and 100° C., respectively, by means of an external cooler and by heating.

The content of N-methyl-MDA in the resulting polyamine was 0.35%.

This polyamine was reacted with phosgene in accordance with a usual cold and warm two-stages process to obtain a polyisocyanate. The content of a hydrolyzable chlorine compound in this polyisocyanate was 0.42%.

COMPARATIVE EXAMPLE 4

The same reactor as in Example 1 was used.

The first stage of the reactor was fed with 95% aniline at 345 g/hr, 35% hydrochloric acid at 165 g/hr and 30% formalin at 111 g/hr (70% of the total formalin), and the second stage was fed with 30% formalin at 48 g/hr (30% of the total formalin) by means of a quantitative pump.

Reaction temperatures in the first, second, third and fourth stages were adjusted to 30° C., 30° C., 100° C. and 100° C., respectively, by means of an external cooler and by heating.

Three hours after the feed start of the raw materials, a solid was formed in the second reactor, so that the feed of formalin was stopped.

What is claimed is:

1. A process for preparing a methylene-crosslinked polyarylamine by reacting aniline with formalin in the presence of hydrochloric acid under the following conditions (a), (b), (c) and (d):
    (a) the amount of hydrochloric acid is in the range of from 0.1 to 0.5 mole per mole of aniline;
    (b) the amount of aniline is in the range of from 1.5 to 4.0 moles per mole of formalin;
    (c) the reaction is divided in at least four stages, and
        the reaction in the first stage is carried out at 20 to 50° C. in a water/aniline ratio in the range of from 1.3 to 2.5 moles,
        the reaction in the second stage is done at 40 to 70° C. in a water/aniline ratio in the range of from 1.9 to 5.0 moles,
        the reaction in the third stage is done at 50 to 90° C. in a water/aniline ratio in the range of from 2.4 to 5.7 moles, and
        the reaction in the last stage is done at a temperature of 110° C. or more; and
    (d) formalin is divided into 3 or more stages and used in the reactions in the respective stages.

2. The process for preparing a methylene-crosslinked polyarylamine according to claim 1 wherein prior to being fed to the first stage, formalin is mixed with hydrochloric acid, and in the second et seq. stages, formalin is fed to each reaction system in the concentration range of from 10 to 25%.

* * * * *